(12) United States Patent
Shepard et al.

(10) Patent No.: US 11,617,890 B2
(45) Date of Patent: *Apr. 4, 2023

(54) FLEXIBLE COMPLEMENTARY METAL-OXIDE-SEMICONDUCTOR PROBES FOR CHRONIC, LARGE-SCALE NEURAL STIMULATION AND RECORDING

(71) Applicant: The Trustees of Columbia University in the City of New York, New York, NY (US)

(72) Inventors: Kenneth L. Shepard, Ossining, NY (US); David Tsai, New York, NY (US); Hongki Kang, South Korea (KR); Jordan Thimot, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/068,229

(22) Filed: Oct. 12, 2020

(65) Prior Publication Data

US 2021/0308468 A1 Oct. 7, 2021

Related U.S. Application Data

(63) Continuation of application No. 15/906,206, filed on Feb. 27, 2018, now Pat. No. 10,799,705, which is a
(Continued)

(51) Int. Cl.
*A61N 1/372* (2006.01)
*A61B 5/00* (2006.01)
(Continued)

(52) U.S. Cl.
CPC ........ *A61N 1/37223* (2013.01); *A61B 5/0031* (2013.01); *A61B 5/291* (2021.01);
(Continued)

(58) Field of Classification Search
CPC .............. A61N 1/37223; A61N 1/0529; A61N 1/0531; A61N 1/0551; A61N 1/3787;
(Continued)

(56) References Cited

U.S. PATENT DOCUMENTS 5,626,630 A * 5/1997 Markowitz ........... A61B 5/1112
128/903
8,332,052 B1 * 12/2012 Orinski ................ A61N 1/0541
607/57

(Continued)

OTHER PUBLICATIONS

International Search Report dated Nov. 14, 2016 in International Application No. PCT/US16/49278.

*Primary Examiner* — Catherine M Voorhees
(74) *Attorney, Agent, or Firm* — Hunton Andrews Kurth LLP (57) ABSTRACT

Systems and methods for providing neural stimulation and recording on a subject using flexible complementary CMOS probes are provided. Disclosed systems can include a flexible probe adapted for insertion into a portion of a brain of the subject, the flexible probe comprising a tail portion and a head portion. The tail portion can include a plurality of electrodes configured to be coupled to the brain and a plurality of front-end amplifiers. Each of the plurality of front-end amplifiers can be configured to amplify a signal received from a corresponding electrode of the plurality of electrodes. The head portion can include one or more inductors configured to enable two-way communication with a wireless reader through a near-field inductive link.

22 Claims, 6 Drawing Sheets

Related U.S. Application Data continuation-in-part of application No. PCT/US2016/049278, filed on Aug. 29, 2016.

(60) Provisional application No. 62/210,532, filed on Aug. 27, 2015.

(51) Int. Cl.
*A61N 1/05* (2006.01)
*A61B 5/291* (2021.01)
*A61N 1/378* (2006.01)
*H04B 5/00* (2006.01)

(52) U.S. Cl.
CPC .......... *A61B 5/7225* (2013.01); *A61N 1/0529* (2013.01); *A61N 1/0531* (2013.01); *A61N 1/0551* (2013.01); *A61N 1/3787* (2013.01); *A61B 2560/0219* (2013.01); *H04B 5/0081* (2013.01)

(58) Field of Classification Search
CPC ..... A61B 5/0031; A61B 5/291; A61B 5/7225; A61B 2560/0219; H04B 5/0081
See application file for complete search history.

(56) References Cited

U.S. PATENT DOCUMENTS

| | | | |
|---|---|---|---|
| 9,662,498 B1* | 5/2017 | Son | C23C 16/26 |
| 10,799,705 B2* | 10/2020 | Shepard | A61N 1/3787 |
| 2006/0265039 A1 | 11/2006 | Bartic et al. | |
| 2007/0106143 A1* | 5/2007 | Flaherty | A61N 1/0531 607/116 |
| 2009/0157141 A1 | 6/2009 | Chiao et al. | |
| 2011/0301665 A1* | 12/2011 | Mercanzini | A61B 5/6868 607/45 |
| 2012/0065699 A1* | 3/2012 | Bedenbaugh | A61N 1/0534 607/45 |
| 2012/0095531 A1* | 4/2012 | Derbas | H01F 5/003 343/866 |
| 2013/0260676 A1* | 10/2013 | Singh | H04B 5/0037 307/104 |
| 2014/0039290 A1* | 2/2014 | De Graff | H01L 27/14632 600/377 |
| 2014/0288667 A1* | 9/2014 | Oxley | A61B 5/377 607/45 |
| 2015/0165206 A1* | 6/2015 | Venkatesan | A61N 1/36139 607/62 |
| 2015/0374990 A1 | 12/2015 | Fan | |
| 2016/0331994 A1* | 11/2016 | Smith | A61N 5/0601 |
| 2020/0155828 A1* | 5/2020 | Shepard | A61B 5/291 |

* cited by examiner

FLEXIBLE COMPLEMENTARY METAL-OXIDE-SEMICONDUCTOR PROBES FOR CHRONIC, LARGE-SCALE NEURAL STIMULATION AND RECORDING

CROSS REFERENCE TO RELATED APPLICATION

This application is a continuation of U.S. patent application Ser. No. 15/906,206 filed on Feb. 27, 2018, which relates to, claims the benefit and priority from, and is continuation-in-part of International Patent Application No. PCT/US2016/049278 filed on Aug. 29, 2016, which claims the benefit and priority from, U.S. Provisional Patent Application No. 62/210,532 filed on Aug. 27, 2015, entitled "Flexible Complementary Metal-OxideSemiconductor Probes for Chronic, Large-Scale Neural Stimulation and Recording," the entire disclosure of which are incorporated herein by reference.

STATEMENT REGARDING FEDERALLY FUNDED RESEARCH

This invention was made with government support under W911NF-12-1-0594 awarded by the Army Research Office. The U.S. government has certain rights in this invention.

BACKGROUND

Certain penetrating electrode technologies, such as the Utah arrays, can provide an interface between electronics and a small area of the cortex. These electrode arrays, which can have penetrating shanks with an electrode, can construct neural interfaces using ultra-wide-band radio links and battery power. Other penetrating technologies integrate multiple electrodes per probe. Some penetrating electrode technologies can reduce the size of the penetrating shank to reduce tissue damage during insertion. Due to the size of the inserted shanks and inability of the rigid electrodes to accommodate brain tissue movements, gliosis and other inflammatory responses can occur. As a result, certain penetrating electrode arrays typically can operate for less than a year before their signal to noise ratio degrades. Furthermore, these electrode arrays can require an open and invasive craniotomy window for wire connections throughout experiments with the cortex.

The challenges of chronic recording, due to aforementioned through-skull, rigid, electrode arrays, can be exacerbated in certain high-density technologies. Techniques to make high-density probes less invasive are needed, through smaller physical size, flexible fabrication material, and high-data-rate wireless telemetry and powering through the skull.

While flexible electrodes can lower tissue injury and irritation, the quality and performance of the electronics in these flexible electrode technologies can be lower than that available in certain commercial complementary metal-oxide-semiconductor (CMOS) technologies. For example, integration densities in flexible electrode technologies can be modest and limit the performance and complexity of circuits designed using such conventional flexible electrode technologies. Flexible electrodes can be fabricated from polyimide substrates and dissolvable silk, and rely on external measurement electronics for signal amplification. In such flexible electrodes, the connection wires in-between can be a limiting factor in scaling up channel density. Additionally, interconnection with flexible electrode arrays can remain a challenge because of limited substrate flexibility and the need to tether wires through the skull.

Accordingly, there is a need for flexible CMOS probes with high electrode densities that can be interfaced with the cortex with reduced invasiveness and without the need to tether wires through the skull.

SUMMARY

In a first aspect of the present disclosure, systems for providing neural stimulation and recording using flexible complementary CMOS probes are provided. According to aspects of the present disclosure, the head of the probe can include an antenna to establish a near-field inductive link through the skull. Using the inductive link, the disclosed neural probe can be wirelessly powered with wireless data telemetry and can eliminate the need for percutaneous wires. The antenna of the disclosed subject matter can fold over the outer surface of the cortex subdurally at the insertion point. Additionally, the integration of active amplifiers directly at the electrodes helps to improve signal fidelity in the disclosed probe.

Flexible electronics can be fashioned with certain fabrication techniques to improve electrode density. Such flexible electronic devices can incorporate multiplexing and front-end amplification circuits.

In some embodiments, the probe can include a head portion and a tail portion on which a scalable number of CMOS electrodes and amplifiers can be placed. The head portion can include one or more power extracting circuits, one or more inductors configured to communicate wirelessly with the reader, one or more signal conditioning circuits, and one or more data conversion circuits. The reader can include a printed circuit board supporting a field-programmable gate array.

In some embodiments, the probe can be powered wirelessly from the reader through a near-field inductive link between an inductor on the head portion of the probe and the reader. Energy can be transferred through near-field backscattering in the high MHz to low Ghz frequency range. The energy harvested from the reader by the probe can be rectified and boosted by the one or more power extracting circuits on the head portion of the probe and used to power the entire probe. The probe can also perform two-way data communication with the reader through the near-field inductive link, which can allow the probe to remain untethered. The probe can communicate with the reader using low power backscattering techniques such as amplitude shift keying, frequency shift keying, or on-off keying which can be performed under the control of a data encoder/modulator circuit in the probe. The head of the probe can include all of the data conversion and powering circuitry, which can be disposed under the inductor and/or inductors.

In accordance with an exemplary embodiment, a plurality of probes can communicate with the reader. Each probe can use a different carrier frequency from the other probes to communicate simultaneously with the reader at the same time as the other probes, which can allow for scalability in the number of probes to be used in conjunction with the reader. Each probe can cover a different area of the cortex such that the simultaneous use of the plurality of probes with the reader can allow for studies of coordinated neural activity across a plurality of different brain areas.

In an exemplary embodiment, the tail portion of the probe can include an arrayed biopotential architecture including one or more analog signal chains for multichannel communication between the circuits proximate the head portion and the electrodes proximate the tail portion. Each analog signal chain can support sampling at the pixel level. In some embodiments, the tail portion can support a plurality of different levels of interconnect metal. Each analog signal chain can include, for example and as embodied herein, a two-transistor first-stage amplifier, a low pass filter, sample and hold circuitry. Signals from a plurality of different analog signal chains can be multiplexed and amplified using a shared amplifier.

DETAILED DESCRIPTION

Systems and methods for performing chronic, large-scale neural stimulation and recording are described herein. According to aspects of the present disclosure, the disclosed subject matter can include a flexible probe configured to be inserted into a cortex and a wireless reader placed proximate the skull and configured to communicate wirelessly with the probe. The flexible probe can survive a maximum bending strain of 1% for a given radius of curvature. For example, for a shank having a thickness of 8 microns at 1% bending strain, a 90° bend in the shank can be achieved in approximately 400 microns of the shank length. In some embodiments, the maximum permissible radius between the reader and the probe can be proportional to the wavelength of the RF wave in tissue in the low GHz range. In some exemplary embodiments, depending upon the tissue and exact frequency used, such a permissible radius between the reader and the probe can range from about 1-5 mm. To meet this radius requirement, the reader can be placed directly on the surface of the skull. The neural probe can support high densities of electrodes along a tail portion of the probe. For example, 256 electrodes can be placed on a 3.2-mm-long tail portion. In some exemplary embodiments, electrode densities can range in excess of 100,000 electrodes/mm$^3$, with an electrode-to-neuron ratio greater than 1. In some embodiments, the electrode density can be increased by several orders of magnitude through the introduction of CMOS integrated circuits, with tightly packaged silicon nanofabricated electrode probes.

Figures 1A, 1B:
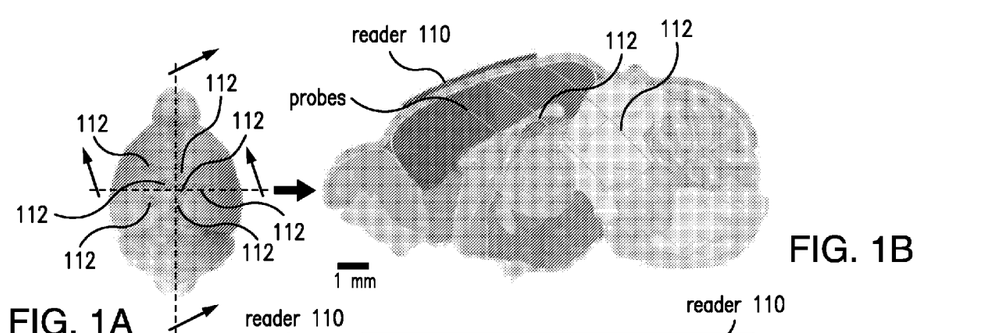
FIGS. 1A-D illustrate an exemplary system for neural stimulation and recording, in accordance with one or more embodiments.
Figure 1C:
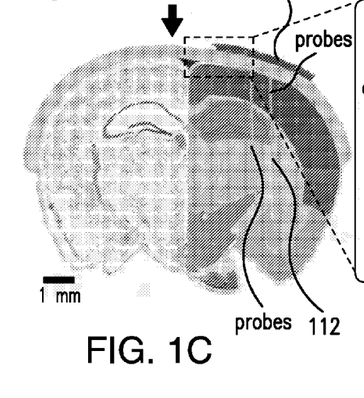
Figure 1D:
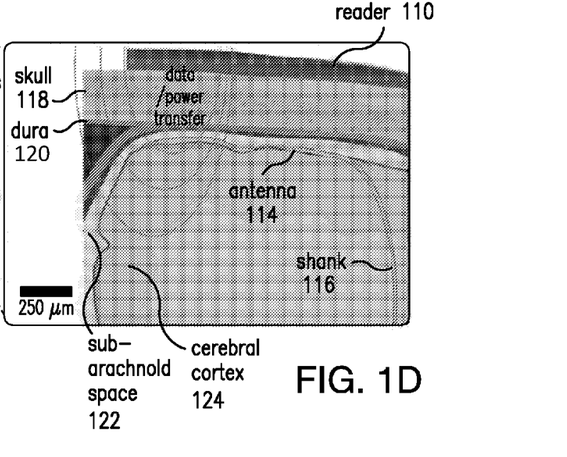

FIGS. 1A-D illustrate an exemplary system for neural stimulation and recording. The exemplary embodiment depicted in FIGS. 1A-D describes the exemplary system being implanted in a subject's brain. The subject can be any animal or human subject, the brain of which is implanted with the disclosed flexible probes. FIG. 1A illustrates a top view of a brain in which probes 112 are inserted. FIG. 1B illustrates a side view and FIG. 1C illustrates a cross-section view of the brain implanted with the disclosed probes 112 and a wireless reader 110 that is positioned above the skull to wireless communicate with the integrated circuits (ICs) in probes 112. FIG. 1D illustrates a magnified view of a portion of FIG. 1C. The head of the probes 112 can be oriented subdurally to communicate with the external wireless reader 110. The probes 112 can be inserted in arbitrary locations and orientations with multiple probes 112 communicating with a single reader 110. In order to prevent large electromagnetic interference between flexible probes, the probes can be placed a minimum of 1 wavelength (e.g., 1-5 mm in this frequency range) apart. The flexible probe head can be fabricated using a thick (e.g., 3+µm) top layer metal for improved coupling efficiency and current density requirements.

In some embodiments, the tail portion of each probe 112 can be inserted into the cortex with the head portion of a probe 112 folding over the outside of the cortex subdurally to position an inductor to communicate with near-field inductive coupling to the reader 110 located outside the skull 118 as shown in FIG. 1D. In some embodiments, the flexible probe can require 5 mW of power in steady state operation. In some embodiments, at a separation distance of 1 mm (e.g., assuming that muscle tissue is the primary medium separating the systems), the power transfer efficiency of the inductive coupling can be about 0.25-0.5%. Such a power transfer efficiency can provide a power requirement of 1-2 W with expected power dissipation from the inductor in the reader. The reader 110 can be a conventional circuit that is packaged using conventional CMOS technology. A small printed-circuit board can support the reader IC including a field-programmable gate array (FPGA) for digital processing and interfacing. In some embodiments, the reader 110 can communicate with the probes 112 or wireless interface, as illustrated in FIGS. 1A-D. In some embodiments, a wired connection can be employed between the reader 110 and the probes 112.

In some embodiments, and as illustrated in FIG. 1D, the antenna 114 of the probe 112 can be placed at the edge of the cerebral cortex 124 and under the sub-arachnoid space 122. The antenna 114 of each probe 112 can wirelessly communicate data and be powered wirelessly through the reader 110 across the skull 118 and the dura 120. The tail portion and/or shank 116 of each probe can include ICs to collect data from the cerebral cortex 124 and can be positioned deeper in the cerebral cortex 124, as shown in FIG. 1D.

In some embodiments, the probes 112 can cover multiple brain areas simultaneously, such as multiple cortical regions, the hippocampus, and thalamus, and numerous subcortical structures, enabling a quantitative study of the coordinated activation across brain areas.

Figure 2:
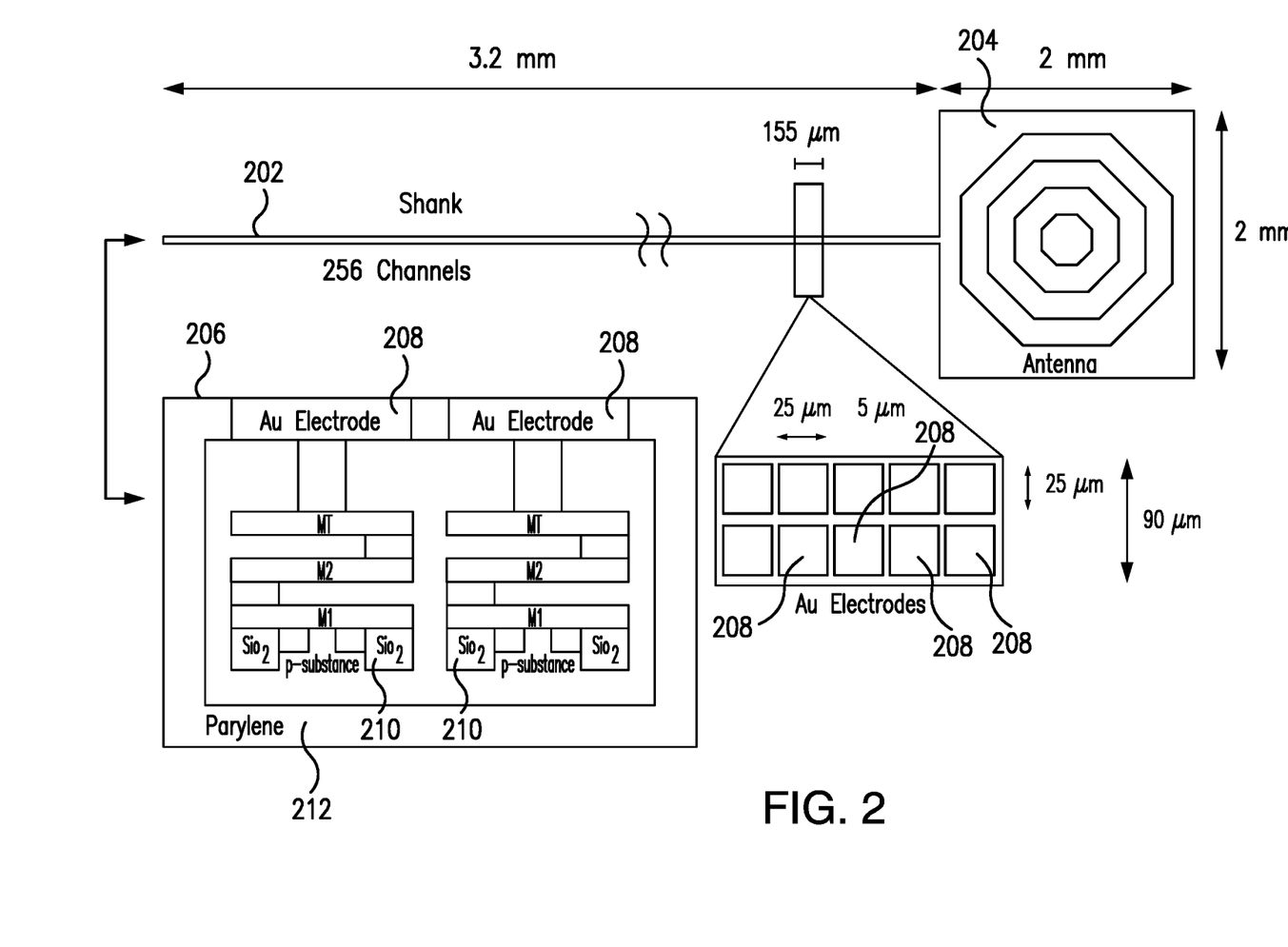
FIG. 2 illustrates an exemplary view of the disclosed flexible probe showing a cross section of a tail portion of the disclose probe, in accordance with one or more embodiments.

FIG. 2 illustrates an exemplary view of the disclosed flexible probe 112 in FIG. 1 and shows a cross section of a tail portion of the disclose probe. In some embodiments, as shown by FIG. 2, the extremely scaled, untethered "tissue-paper-like" probe 112 can include a 2-mm-by-2-mm head portion including one or more antennas 204. The antennas 204 can be integrated inductors. The probe 112's tail portion 202, also referred to as the shank, can serve a scalable number of electrodes 208. The probe 112's tail portion 202 can also contain the front-end amplifiers. In the exemplary embodiment of FIG. 2, the tail portion 202 can have a cross section of 90 μm by 3.2 mm. Multiple different electrodes can be positioned throughout the length of the tail portion 202. The tail portion 202 can include multiple (e.g., 256) channels of analog signal chain circuits with each channel containing multiple circuits in contact with a gold electrode 208. While the gold electrode 208 can interface with the cerebral cortex 124, the circuits in each channel can process information collected by each of the multiple electrodes 208 and prepare that data for transmission to the reader 110 through the antenna 204.

As illustrated by the exemplary embodiment of FIG. 2, the tail portion 202 can be coated with a parylene layer 212. Portion 206 of the tail portion 202 illustrates a cross-section view of a a segment of the tail portion 202, which can be 8 microns thick. As illustrated in portion 206, gold electrodes 208 can be in contact with multiple (e.g., 3) metal layers in communication with a CMOS transistor 210.

In some embodiments, the CMOS transistor 210 can be an n-type field effect transistor (nFET) with n-type source and drain regions in a p-type semiconductor substrate. In some embodiments, the metal gates that can be insulated from the semiconductor by a layer of SiO2 or other dielectric. In some embodiments, the metal layers can include other circuit elements such as power extracting, signal conditioning, and data conversion circuits in communication with the CMOS transistor 210 that receives information from each electrode 208. Each electrode 208 can provide information from the cerebral cortex 124 that can modulate and/or control the operation of the CMOS transistor 210 and the corresponding power extracting, signal conditioning, and data conversion circuits in each channel. For example, each electrode can be electrically coupled to a CMOS transistor 210's gate terminal and can provide the signal received from cerebral cortex 124 as an input to the gate terminal to control the operation of the CMOS transistor 210.

In some embodiments, each of the CMOS transistors 210 can be a part of the front-end amplifiers that are electrically coupled to each electrode in the flexible probe 112. In some embodiments, each of the plurality of analog signal chain circuits can include the front-end amplifier including the CMOS transistor 210. The other circuit elements of each of the analog signal chains can be located on the metal layers located above the CMOS transistors 210. Each flexible probe 112 can include multiple (e.g., upto 1024) such channels.

In some embodiments, the RF data and telemetry exchanged between the reader 110 and each probe 112 can be supported by a dense (>7000 mm$^{-2}$) array of on-chip electrodes on the tail portion 202 of the probe 112. The use of CMOS technology in these probes 112 can dramatically increase the electrode density possible without sacrificing electrical performance. The resulting electrode density allows spikes to be isolated and allows the extent of the dendritic field to be determined by identifying the adjacent electrodes recording the same spike. The architecture of the probe circuitry can be modular, allowing longer and/or shorter probes with more or less electrodes to be easily designed.

Figures 3A, 3B:
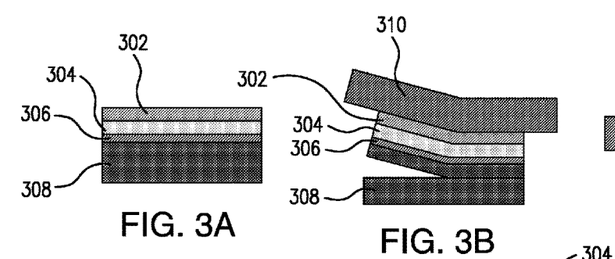
FIGS. 3A-F illustrate an exemplary spalling process for producing the flexible CMOS circuits of the disclosed probe, in accordance with one or more embodiments.
Figure 3C:
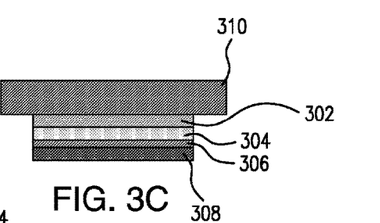
Figure 3D:
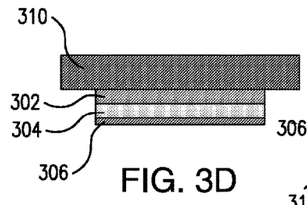
Figure 3E:
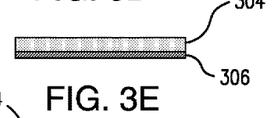
Figure 3F:
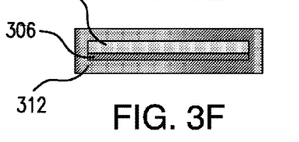

FIGS. 3A-F illustrate an exemplary spalling process for producing a tissue-paper-like ultra-thin flexible probe 112. In FIG. 3A, a nickel stressor layer can be deposited on top of a circuit layer 304 that is deposited on a silicon oxide (SiO2) layer 306 and/or other dielectric layer that is deposited on a silicon substrate 308. In FIG. 3B, spalling process can be performed with the addition of a handle 310 on top of the nickel stressor layer 302. FIG. 3C shows the spalled circuit. In FIG. 3D, hydroxyl etch can be performed on the back of the remaining silicon substrate 308 to the buried oxide to remove the substrate 308. In FIG. 3E, the handle 310 and the nickel stressor layer 302 can be removed. In FIG. 3F, the remaining circuit layer 304 and the silicon oxide layer 306 can be encapsulated with parylene.

In some embodiments, prior to spalling or any chip thinning process, the CMOS circuits 210 for the probe 112 can be post-processed to replace the top-level aluminum interconnect level at the probes with gold and/or platinum electrodes. In some embodiments, at the same time, the etching of the thickest top level interconnect from the tail of the probe can allow this part of the probe to be thinned to less than 8 microns. In some embodiments, the head of the probe, which will contain thick inductor metallization, can be be approximately 12 microns thick. In some embodiments, parylene-C can then be deposited on both sides of the probe at a thickness of approximately 50 nm to provide passivation. On the top surface, lithographic patterning can be used to make sure that the electrodes themselves are not passivated, as shown in FIG. 3.

Additionally or alternatively, probes 112 can also be fabricated by a sequential combination of other techniques such as mechanical grinding, chemical-mechanical polishing (CMP), and wet/dry etching.

Figure 4:
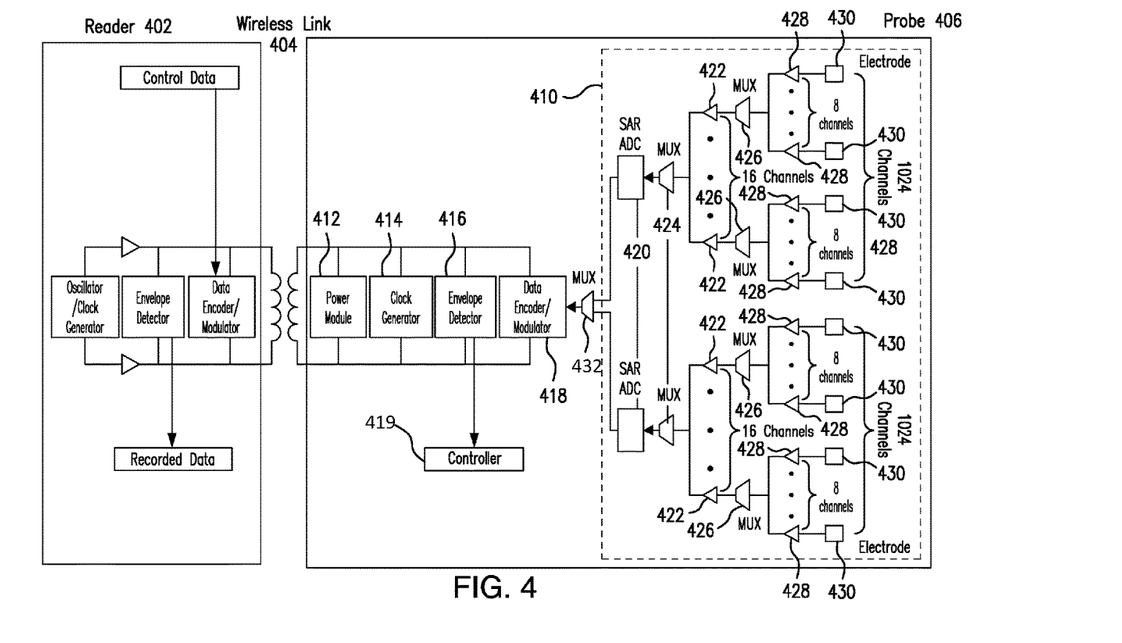
FIG. 4 illustrates an exemplary system level block diagram of the reader and the probe, in accordance with one or more embodiments.

FIG. 4 illustrates an exemplary system level block diagram of the reader 402 and a probe 406. Reader 402 can correspond to the wireless reader 110 described in connection with FIGS. 1-2 and probe 406 can correspond to the probe 112 described in connection with FIGS. 1-2. The reader 402 can be wirelessly coupled with the probe 406 through a wireless link 404. For example the reader 402's antenna can communicate wirelessly with the probe 406's antenna or antennas through the wireless link 404.

In some embodiments, the circuitry 410 of the probe 406 shown in FIG. 4 can be placed on the shank and/or tail portion of the probe 406. As illustrated in the exemplary embodiment shown in FIG. 4, the 256 channels of the analog signal chain in circuitry 410 can be time-multiplexed up the shank of the probe 406 to produce two channels that can feed data converters on the head portion of the probe 406.

In the exemplary embodiment shown in FIG. 4, the circuitry 410 can include multiple (e.g., 1024) electrodes 430 on a probe 406. The signal measured from each of the multiple electrodes 430 can be fed into a corresponding front-end amplifier 428, which can amplify the signal collected by the electrodes 430. The amplified output of the front-end amplifiers 428 can be multiplexed by the multiplexers 426. Each of the multiple multiplexers 426 can multiplex a plurality of signal outputs from a corresponding set of front-end amplifiers 428. The multiplexed signal output from the multiplexers 426 can then be further amplified by a corresponding amplifier 422. The amplified signal output of the amplifiers 422 can be multiplexed by the multiplexers 424. Each of the multiple multiplexers 424 can multiplex a plurality of signal outputs from a corresponding set of amplifiers 422. The multiplexed signal outputs of multiplexers 424 can be converted from analog signal to a digital signal by one or more successive-approximation (SAR) analog-to-digital converters (ADCs) 410, each of which can operate at 10 bits at a sample rate of 4.2 MSa/s and providing 56 Mbps overall data rate. Slight oversampling can help to improve alias rejection. An SAR ADC 420 can be chosen because it can achieve very low power operation because of amplifier-less implementations. In some embodiments, ADCs 420 and associated digital processing can dissipate up to 2 mW of power. The metalinsulator-metal capacitors of the charge redistribution digital-to-analog converter required for the SAR ADC can be configured under the inductor to minimize overall probe head area. The output of the SAR ADCs 420 can be multiplexed by the multiplexer 432. The multiplexed digital signal output of the multiplexer 432 can be input into the data encoder/modulator 418, which can be located in the head portion of the probe 406.

In some embodiments, the power module 412, clock generator 414, envelope detector 416, data encoder/modulator 418, and the controller 419 can be located at the head portion of the probe 406. In some embodiments, the electrodes 430, front-end amplifiers 428, amplifiers 422, multiplexers 426, multiplexers 424, multiplexer 432 and SAR ADC 420 can be located at the tail portion of the probe 406.

In some embodiments, the disclosed subject matter can use near-field backscatter in the high MHz to low GHz regime for both power and data transfer with antenna coils of millimeter scale. In some embodiments, the low MHz regime can be utilized for power transfer, and the high MHz and low GHz regime can be utilized for data transfer. Use of near-field backscatter for power and data transfer can permit the head of the ultra-thin probes to have a 2-mm-by-2-mm form factor.

In some embodiments, the probe 406 can be powered through the near-field coupling of the reader 402 to the probe 406. In some embodiments, energy can be transferred to the probe 406 at a frequency between about 500 MHz and 1 GHz for data telemery. In some embodiments, energy for powering purposes can be transferred to the probe 406 at a frequency range between about 10 MHz and 1 GHz. In some embodiments, a coupled inductor topology with millimeter-scale inductors for the reader 402 and probe 406's anntennae with a resonance frequency of 0.9 GHz for the brain can can allow for approximately 0.5% of power transferred from reader to probe when the system is matched for maximum power transfer, assuming a skull that is 250 microns thick, a dura that is 20 microns thick (e.g., a mouse brain), and the remaining 730 micron spacing is muscle-based tissue. The approximately 1 W of power that is required to be delivered by the reader 402 to power the probe 406 can be less than that of certain cell phones and can result in much less than 1° C. of heating of the mouse brain and below the 10 W/kg specific absorption requirement.

In some embodiments, the harvested energy can be rectified and boosted with proper voltage limiting by the power module 412 to provide the supply voltage for running the entire probe 406. In order to prevent problems with misalignment and to enable one reader 402 to interact with multiple probes 406, the external radius of the reader coil can be made larger than the probe 406's coil as part of coil optimizations since the reader coil does not carry the same severe form-factor limitations as the probe coil. The internal radius of the two coils can still be matched as closely as possible. Signal diversity to prevent signal interference amongst multiple probes 406 inserted in a target brain that communicate with the same reader 402 can be provided by employing slightly different carrier frequencies in each probe 406. This architecture can be scalable in several different ways. Since there is no limit to the number of individual probes that can be inserted as long as wavelength spacing is observed, insertion can proceed with each probe 406 in any orientation and spacing desired as shown in FIG. 1. In some embodiments, probe spacing can be small enough such that multiple probes 406 can communicate with the same reader.

In some embodiments, data transmission can occur using low-power backscatter techniques, such as those employed in RFID, with either amplitude shift keying (ASK), On-Off keying (OOK) or frequency shift keying (FSK) under the control of the data encoder/modulator 418 shown in FIG. 4. In some embodiments, the data encoder/modulator 418 can dissipate an additional 1 mW of power. The head of the probe 406 can contain all the data conversion and powering circuitry (e.g., power module 412, clock generator 414, envelope detector 416, data encoder/modulator 418, and controller 419). The envelope detector 416 can provide the controller 419 with information necessary to control the data conversion and/or powering operations. The data conversion and powering circuitry (e.g., power module 412, clock generator 414, envelope detector 416, data encoder/modulator 418, and controller 419) can be built under the inductor of the probe antenna to conserve area and can be robust in the presence of any electromotive forces (EMFs) induced in interconnects due to the magnetic fields emanating from the reader 402.

In some embodiments, the reader 402 can include an oscillator/clock generator, envelope detector, and data encoder/modulator circuits to interpret the encoded data received from the probe 406. The reader 402's envelope detector circuit can produce recorded data and the reader 402's data encoder/modulator circuit can receive, as input signals, control data.

In exemplary embodiments, to enable two-way electrical communication, the shank of the probe 406 can be capable of electrically stimulating the brain. Stimulus requirements for implantable devices can take the form of constant current mode or constant voltage mode stimulation.

In some embodiments, front-end amplification and a programmable low-pass cut-off of the signal received from the electrodes in each probe can be provided by the circuits described in FIG. 5 or FIG. 6. In these circuit designs, as in the CMOS imagers, the sampling can be moved to the pixel level, occurring right after the first gain stage.

Figure 5A:
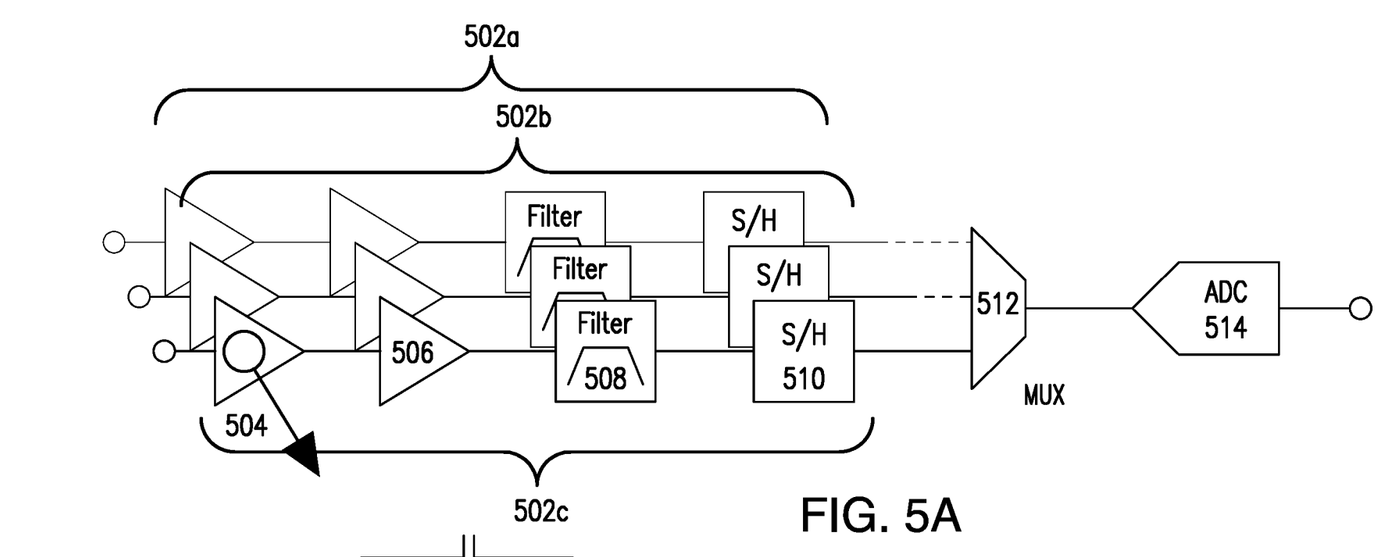
FIGS. 5A-B illustrate exemplary circuit diagrams of a multichannel biopotential architecture of the disclosed probe in which multiple parallel channels are time-multiplexed at the end of the analog gain chain before data conversion, in accordance with one or more embodiments.

FIGS. 5A-B illustrate exemplary circuit diagrams of a multichannel biopotential architecture of the disclosed probe in which multiple parallel channels are time-multiplexed at the end of the analog gain chain before data conversion. As shown in FIG. 5A, multiple parallel channels 502*a*, 502*b*, and 502*c* can be time-multiplexed, using multiplexer 512, and inputted into an analog to digital converter (ADC) 514. Each channel's analog gain chain (e.g, 502*a*, 502*b*, and 502*c*) can include front end amplifiers 504 and 506. The outputs the front end amplifiers 504 and 506 can be filtered using a programmable filter 508 and then can be fed into a sample/hold circuit 510. The sample/hold circuit 510 can sample the voltage of a continuously varying analog signal received from the electrodes of the probe and hold (e.g., lock and/or freeze) its value at a constant level for a specified minimum period of time to eliminate variations in input signal that can corrupt the analog to digital conversion process. The output of the sample/hold circuit 510 can be time-multiplexed along with the similar outputs from the other parallel channels at multiplexer 512 and outputted to the ADC 514.

Figure 5B:
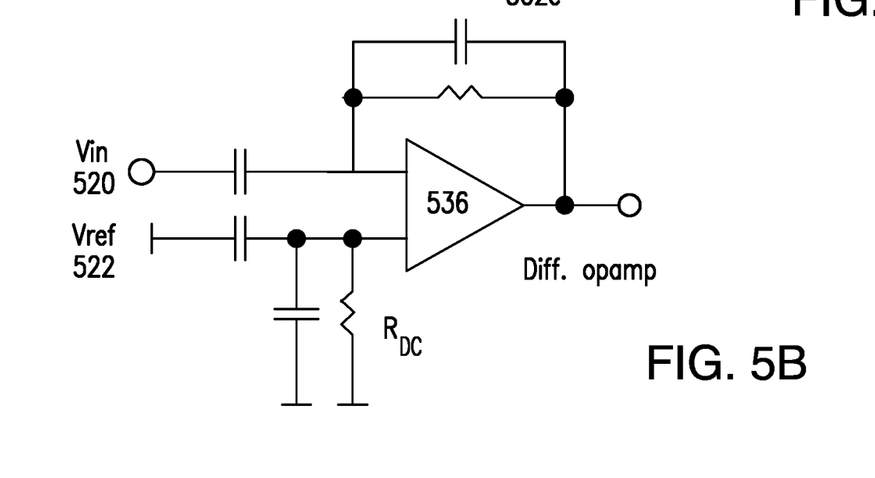

FIG. 5B illustrates the circuitry of the front-end amplifier 504 in greater detail. The measured signal from the cerebral cortex by an electrode, such as electrode 208 of FIG. 2, can be received as an input voltage 520 to the front-end amplifier 504 and compared against a reference voltage 522 using a differential operational amplifier 536 with a feedback path.

Figure 6A:
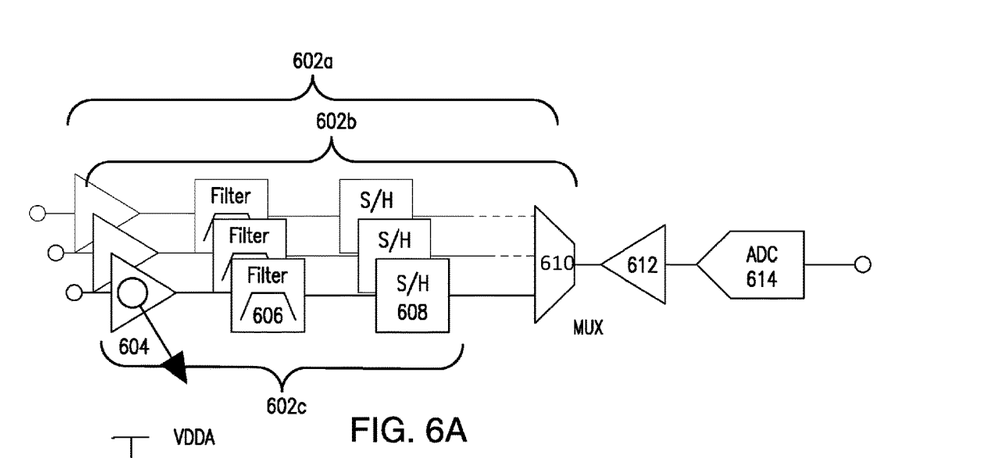
FIGS. 6A-B illustrate exemplary circuit diagrams of a multichannel biopotential architecture of the disclosed probe with an arrayed architecture in which sampling occurs at the pixel level, in accordance with one or more embodiments.
Figure 6B:
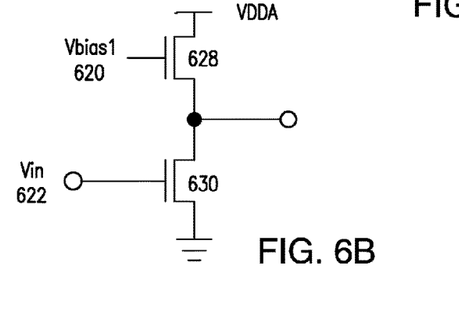

FIGS. 6A-B illustrate exemplary circuit diagrams of a multichannel biopotential architecture of the disclosed probe with an arrayed architecture in which sampling occurs at the pixel level.

As shown in FIG. 6A, multiple parallel channels 602a, 602b, and 602c can be multiplexed, using multiplexer 610, and inputted into an analog to digital converter (ADC) 614. Each channel's analog gain chain (e.g., 602a, 602b, and 602c) can include a front end amplifier 604. The outputs of the front end amplifier 604 can be filtered using a programmable filter 606 and then can be fed into a sample/hold circuit 608. The sample/hold circuit 608 can sample the voltage of a continuously varying analog signal received from the electrodes of the probe and hold (e.g., lock and/or freeze) its value at a constant level for a specified minimum period of time to eliminate variations in input signal that can corrupt the analog to digital conversion process. The output of the sample/hold circuit 608 can be multiplexed along with the similar outputs from the other.

FIG. 6B illustrates the circuitry of the front-end amplifier 604 in greater detail. The measured signal from the cerebral cortex by an electrode, such as electrode 208 of FIG. 2, can be received as an input voltage 622 to the front-end amplifier 604. In the embodiment illustrated in FIGS. 6A-B, the first amplifier 604 can be made as simple as possible, usually reduced to a few transistors (e.g., transistors 628 and 630). If a reference comparison voltage is necessary, this can usually be accomplished indirectly through a bias control voltage 620 ($V_{bias}$) on the amplifying transistor 628.

In the embodiment shown in FIGS. 6A-B, significant multiplexing can occur prior to the next stage of amplification that is performed at amplifier 612. Data conversion can then follows at the end of the analog gain chain at the ADC 614. The biopotential circuit architecture of FIGS. 6A-B can provide significant area and power savings by sharing the same amplifiers over multiple channels and keeping the first-stage amplifier 604, which is not shared, simple and dense.

Unlike rigid recording electrodes, the disclosed flexible electrodes, both penetrating and subdural, can maintain signal quality over long periods of time and lower tissue injury and irritation. In some embodiments, once the disclosed flexible probe is inserted into the brain, the probe can experience reduced gliosis and inflammation compared to certain conventional probes due to the extreme flexibility and small physical extent of the disclosed flexible probe.

In accordance with another aspect of the disclosed subject matter, the disclosed subject matter can be designed in conventional CMOS technology and fabricated in a commercial foundry. The disclosed ultra-thin probe can be rendered, but not limited to, to a total thickness of less than 12 µm through a number of procedures including controlled spalling, mechanical grinding, chemical-mechanical polishing and wet/dry etching, which renders otherwise brittle semiconductors flexible and robust with the consistency of tissue paper. The process can also include passivation by depositing parylene-C, oxides, or multilayers of these materials on both sides of the probe using lithographic patterning; electrodes can be independently processed to incorporate materials such as nobel metals, oxides, TiN, or poly(3,4-ethylenedioxythiophene) polystyrene sulfonate (PEDOT:PSS). The spalling process is performed by depositing a nickel stressor layer on top of the starting wafer. A handle can be added and the resulting structure can be spalled. The process can also include hydroxyl etching of the remaining silicon back to the buried oxide, and the handle and the nickel layer can be removed.

Unless specifically stated otherwise, as apparent from the following discussions, it is appreciated that throughout the specification discussions utilizing terms such as "processing," "computing," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Although one or more embodiments have been described herein in some detail for clarity of understanding, it should be recognized that certain changes and modifications can be made without departing from the spirit of the disclosure. Features of certain embodiments can be combined with features of other embodiments; thus certain embodiments can be combinations of features of multiple embodiments. The embodiments described herein can employ various computer-implemented operations involving data stored in computer systems. For example, these operations can require physical manipulation of physical quantities—usually, though not necessarily, these quantities can take the form of electrical or magnetic signals, where they or representations of them are capable of being stored, transferred, combined, compared, or otherwise manipulated. Further, such manipulations are often referred to in terms, such as producing, yielding, identifying, determining, or comparing. Any operations described herein that form part of one or more embodiments of the disclosure can be useful machine operations. In addition, one or more embodiments of the disclosure also relate to a device or an apparatus for performing these operations. The apparatus can be specially constructed for specific required purposes, or it can be a general purpose computer selectively activated or configured by a computer program stored in the computer. In particular, various general purpose machines can be used with computer programs written in accordance with the teachings herein, or it can be more convenient to construct a more specialized apparatus to perform the required operations.

Although one or more embodiments of the present disclosure have been described in some detail for clarity of understanding, it will be apparent that certain changes and modifications can be made within the scope of the claims. Accordingly, the described embodiments are to be considered as illustrative and not restrictive, and the scope of the claims is not to be limited to details given herein, but can be modified within the scope and equivalents of the claims. In the claims, elements do not imply any particular order of operation, unless explicitly stated in the claims.

Many variations, modifications, additions, and improvements can be made. Plural instances can be provided for components, operations or structures described herein as a single instance. Boundaries between various components, operations and data stores are somewhat arbitrary, and particular operations are illustrated in the context of specific illustrative configurations. Other allocations of functionality are envisioned and can fall within the scope of the disclosure(s). In general, structures and functionality presented as separate components in exemplary configurations can be implemented as a combined structure or component. Similarly, structures and functionality presented as a single component can be implemented as separate components.

These and other variations, modifications, additions, and improvements can fall within the scope of the appended claim(s).

What is claimed is:

1. A system for performing neural stimulation and recording in the nervous system of a subject, comprising:
   a flexible probe comprising a tail portion and a head portion, wherein the tail portion is configured to be inserted into a cerebral cortex of the subject; and
   a single complementary-metal-oxide-semiconductor (CMOS) chip which is included in the flexible probe;
   one or more electrodes integrated into the CMOS chip; and
   one or more devices configured to provide wireless powering and data telemetry.

2. The system of claim 1, further comprising
   a plurality of front-end amplifiers integrated into the tail portion, wherein each of the plurality of front-end amplifiers is configured to amplify a signal received from a corresponding electrode of the one or more electrodes,
   wherein the one or more devices comprises one or more inductors which are configured to enable two-way wireless communication and adapted to be powered using a wireless external device.

3. The system of claim 2, wherein each of the plurality of front-end amplifiers comprises two CMOS transistors, wherein a gate terminal of at least one of the two CMOS transistors is input with the signal received from the corresponding electrode of the one or more electrodes.

4. The system of claim 2, wherein the tail portion comprises (i) a plurality of metal layers and (ii) a plurality of analog signal chain circuits, wherein each of the plurality of analog signal chain circuits comprises one of the plurality of front-end amplifiers.

5. The system of claim 4, wherein each of the plurality of analog signal chain circuits is configured to process the signal received from the corresponding electrode of the one or more electrodes, and wherein signal outputs of at least two of the plurality of analog signal chain circuits are multiplexed, amplified, and converted into a digital signal by an analog to digital converter for transmission to the wireless reader.

6. The system of claim 1, wherein the head portion further comprises:
   data conversion circuitry configured to process signals received from each of the one or more electrodes for transmission to a wireless reader; and
   power extracting circuitry configured to provide the flexible probe with energy received wirelessly from the wireless reader by the flexible probe by rectifying and boosting the received energy from the wireless reader,
   wherein the data conversion circuitry and the power conversion circuitry are disposed under the one or more devices.

7. The system of claim 6, wherein the data conversion circuitry comprises a data encoder circuit configured to use near-field electromagnetic backscattering in a low megahertz to low gigahertz frequency range to enable power transfer and a high megahertz to low gigahertz frequency range to enable the two-way communication between the flexible probe and the wireless reader.

8. The system of claim 6, wherein the head portion of the flexible probe is oriented subdurally to communicate with the wireless reader.

9. The system of claim 1, wherein the one or more electrodes are configured to detect an action potential by identifying an adjacent electrode from the one or more electrodes recording the action potential.

10. The system of claim 1, wherein the tail portion comprises a scalable circuit architecture in which the number of electrodes in the one or more electrodes can be scaled to provide for an electrode to neuron ratio greater than 1.

11. A system for performing neural stimulation and recording in the nervous system of a subject, comprising:
    a plurality of flexible probes, at least one of the flexible probes comprising a head portion and a tail portion, the tail portion being configured to be inserted into a cerebral cortex of the subject;
    a plurality of flexible pliable single complementary-metal-oxide-semiconductor (CMOS) chips which are included in the flexible probes;
    one or more electrodes integrated into each of the plurality of CMOS chips; and
    one or more devices configured to provide wireless powering and data telemetry.

12. The system of claim 11, further comprising
    a plurality of front-end amplifiers, wherein each of the plurality of front-end amplifiers is configured to amplify a signal received from a corresponding electrode of the one or more electrodes; and
    wherein the one or more devices comprises one or more inductors which are configured to enable two-way wireless communication and powering with a wireless reader through a near-field inductive link; and
    the wireless reader is configured to provide power to the plurality of flexible probes and engage in two-way communication with each of the plurality of flexible probes.

13. The system of claim 12, wherein different carrier frequencies are used by each of the plurality of probes to communicate with the wireless reader to prevent signal interference amongst the plurality of probes.

14. The system of claim 12, wherein the head portion of each of the plurality of flexible probes further comprises:
    data conversion circuitry configured to process signals received from each of the one or more electrodes for transmission to a wireless reader; and
    power extracting circuitry configured to provide the flexible probe with energy received wirelessly from the wireless reader by the flexible probe by rectifying and boosting the received energy from the wireless reader,
    wherein the data conversion circuitry and the power conversion circuitry are disposed under the one or more devices.

15. The system of claim 12, wherein each of the plurality of front-end amplifiers of each of the plurality of flexible probes comprises two CMOS transistors, wherein a gate terminal of at least one of the two CMOS transistors is input with the signal received from the corresponding electrode of the one or more electrodes.

16. The system of claim 12, wherein the tail portion of each of the plurality of flexible probes comprises (i) a plurality of metal layers and (ii) on which a plurality of analog signal chain circuits located, and wherein each of the plurality of analog signal chain circuits comprises one of the plurality of front-end amplifiers.

17. The system of claim 16, wherein each of the plurality of analog signal chain circuits of each of the plurality of flexible probes is configured to process the signal received from the corresponding electrode of the one or more electrodes, and wherein signal outputs of at least two of the plurality of analog signal chain circuits are multiplexed, amplified, and converted into a digital signal by an analog to digital converter for transmission to the wireless reader.

18. The system of claim 12, wherein the one or more electrodes of each of the plurality of flexible probes are configured to detect an action potential in a dendritic field of the brain by identifying an adjacent electrode from the one or more electrodes in each flexible probe recording the action potential.

19. The system of claim 12, wherein the tail portion of each of the plurality of flexible probes comprises a scalable circuit architecture in which the number of electrodes in the one or more electrodes can be scaled to provide for an electrode to neuron ratio greater than 1.

20. The system of claim 12, wherein the head portion of each of the plurality of flexible probes is oriented subdurally to communicate with the wireless reader, and wherein the plurality of flexible probes are inserted in arbitrary locations with arbitrary orientations.

21. The system of claim 12, wherein the plurality of flexible probes are configured to be simultaneously inserted into and coupled to a plurality of brain areas to enable a quantitative study of the coordinated activation across the plurality of brain areas.

22. A method for performing for performing neural stimulation and recording on a subject, the method comprising:

inserting a tail portion of at least one of a plurality of flexible probes into a cerebral cortex of a brain of the subject, each of the plurality of flexible probes comprising the tail portion and a head portion, wherein at least one flexible pliable complementary-metal-oxide-semiconductor chip included in the at least one of the plurality of flexible probes,
  wherein the tail portion comprises a plurality of front-end amplifiers, and
  wherein the at least one of flexible probes comprises one or more devices configured to receive power from a wireless reader;
providing, by one or more inductors, power received from the wireless reader to the plurality of flexible probes;
receiving, at the plurality of electrodes, a plurality of signals from the brain of the subject;
amplifying, at each of the plurality of front-end amplifiers, each of the plurality of signals from a corresponding electrode of the plurality of electrodes; and
transmitting, by the one or more devices, the amplified plurality of signals to the wireless reader through a near-field inductive link.

\* \* \* \* \*